US012446882B1

(12) United States Patent
Kimsey et al.

(10) Patent No.: US 12,446,882 B1
(45) Date of Patent: Oct. 21, 2025

(54) SENSORS AND/OR INDICATORS FOR A STAPLING DEVICE

(71) Applicant: Cilag GmbH International, Zug (CH)

(72) Inventors: John Scott Kimsey, Walton, KY (US); Michael Bahan, Cincinnati, OH (US); Kylie Moellering, Cincinnati, OH (US)

( * ) Notice: Subject to any disclaimer, the term of this patent is extended or adjusted under 35 U.S.C. 154(b) by 0 days.

(21) Appl. No.: 18/792,951

(22) Filed: Aug. 2, 2024

(51) Int. Cl.
*A61B 17/115* (2006.01)
*A61B 90/00* (2016.01)
*A61B 90/92* (2016.01)
*A61B 17/00* (2006.01)

(52) U.S. Cl.
CPC .......... *A61B 17/1155* (2013.01); *A61B 90/06* (2016.02); *A61B 90/92* (2016.02); *A61B 2017/00115* (2013.01); *A61B 2090/0807* (2016.02); *A61B 2562/0257* (2013.01)

(58) Field of Classification Search
CPC ...... A61B 17/1155; A61B 90/06; A61B 90/92
See application file for complete search history.

(56) References Cited

U.S. PATENT DOCUMENTS

| | | | |
|---|---|---|---|
| 5,205,459 | A | 4/1993 | Brinkerhoff et al. |
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main |
| 5,350,104 | A | 9/1994 | Main |
| 5,533,661 | A | 7/1996 | Main et al. |
| 8,910,847 | B2 | 12/2014 | Nalagatla et al. |
| 9,161,803 | B2 | 10/2015 | Yates et al. |
| 9,713,469 | B2 | 7/2017 | Leimbach et al. |
| 9,907,552 | B2 | 3/2018 | Measamer et al. |
| 9,936,949 | B2 | 4/2018 | Measamer et al. |
| 10,092,292 | B2 | 10/2018 | Boudreaux |
| 10,226,253 | B2 | 3/2019 | Dinardo |
| 10,478,189 | B2 | 11/2019 | Bear et al. |
| 2015/0083772 | A1 | 3/2015 | Miller |
| 2017/0258471 | A1 | 9/2017 | Dinardo et al. |
| 2018/0132849 | A1 | 5/2018 | Miller et al. |
| 2018/0132853 | A1 | 5/2018 | Miller |
| 2018/0310938 | A1 | 11/2018 | Kluener |
| 2020/0281596 | A1* | 9/2020 | Wise .................. A61B 17/1114 |

* cited by examiner

*Primary Examiner* — Nathaniel C Chukwurah
(74) *Attorney, Agent, or Firm* — Amir Bishara

(57) ABSTRACT

A surgical instrument includes a handle assembly; a rotatable knob disposed at a proximal end portion of the handle assembly; an adjusting rod disposed within the handle assembly, the adjusting rod having a proximal portion, an opposed distal portion, and a medial portion disposed thereinbetween, the medial portion having an outer diameter smaller than the outer diameters of the proximal and distal portions; whereby rotation of the rotatable knob is configured to advance the adjusting rod in a distal direction within the handle assembly or to retract the adjusting rod in a proximal direction within the handle assembly; and a button disposed at side portion of the handle assembly and configured to provide an indication for anastomotic release when a pin extending from the button is disposed towards the medial portion of the adjusting rod.

16 Claims, 11 Drawing Sheets

SENSORS AND/OR INDICATORS FOR A STAPLING DEVICE

FIELD OF THE INVENTION

The present invention is related to a surgical instrument, such as a stapler, for creating an anastomosis in a body lumen. In particular, the present invention is related to a powered stapler for creating an anastomosis in colorectal and/or gastric procedures, including safe removal of the device upon competition of the anastomosis.

BACKGROUND OF THE INVENTION

Creating an anastomosis within a bodily lumen through use of a surgical instrument, such as a powered stapler, may typically involve device indications for preferred stapling configurations for proper anastomosis. After creation of a proper anastomosis, the surgical instrument is removed by a practitioner.

Components of the surgical instrument should be properly configured and arranged or positioned for removal from a patient. Currently there is a need to give clear indication to a practitioner or a user that the device is ready for anastomotic release.

SUMMARY OF THE INVENTION

The present invention provides a surgical instrument which gives a clear indication or indications to a practitioner or user that the device is ready for anastomotic release and/or removal from a patient.

In one aspect of the present invention, a surgical instrument providing a clear indication to a practitioner or user that the device is ready for anastomotic release may include, among other things: a handle assembly having opposed proximal and distal end portions an upper portion, a lower portion having a gripping portion, and opposed first and second side portions; a rotatable knob disposed at the proximal end portion; an adjusting rod disposed within the handle assembly, the adjusting rod having a proximal portion, an opposed distal portion, and a medial portion disposed thereinbetween, the medial portion having an outer diameter smaller than the outer diameters of the proximal and distal portions. The proximal portion of the adjusting rod nay include a first helical groove and a second helical groove. The instrument may also include a projection or thread secured within the housing of the handle assembly and engageable with the first helical groove, whereby rotation of the rotatable knob is configured to advance the adjusting rod in a distal direction within the handle assembly or to retract the adjusting rod in a proximal direction within the handle assembly. The instrument may further include a button disposed at the first side portion, the button having a force-biased, extensible pin extending towards the adjusting rod, the pin having a pin end, when in a partially extended state, is configured to be engageably disposed with the distal portion of the adjusting rod, and the pin end, when in a fully extended state, is configured to be proximally disposed towards, desirably non-engageable, with the medial portion of the adjusting rod.

The button may have a first position, when the pin end is extended, and a second position, when the pin end is not extended, but in a retracted position, where, when the button is in the first position, a visual indication is provided that the surgical instrument is in a configuration for anastomotic release and/or removal from a patient. When in the second position, the button may be extended outside and away from the first side of the handle assembly, and, when in the first position, the button may be partially extended outside and away from the first side of the handle assembly.

A top portion of the button may have a first visual indication or color and a side portion of the button disposed away from the top portion has a second visual indication or color with the first visual indication or color being different from the second visual indication or color; wherein, when the button is in the first position, only the first visual indication or color of the top portion of the button is visible; and wherein, when the button is in the second position, both the first visual indication or color of the top portion of the button and second visual indication or color of the side portion are visible.

The surgical instrument may further include a proximity sensor disposed within the handle assembly, the proximity sensor may be configured to provide an indication when the pin is in the fully extended state or when the device is ready for anastomotic release and/or removal from a patient.

The upper portion of the handle assembly may further include an indicator status window, where the indication that the pin is in the fully extended state or that device is ready for anastomotic release and/or removal from a patient is displayed in the indicator status window.

The surgical instrument may further include: a shaft assembly having a proximal end securably disposed at a distal end of the adjusting rod at the distal end of the handle assembly, a distal end having a staple and knife housing disposed thereat, a sheath disposed between the proximal and distal ends, and a trocar disposed within the sheath and extendable beyond a distal end of the shaft, where advancing the adjusting rod advances the trocar and where retracting the adjusting rod retracts the trocar. The surgical instrument may further include an anvil having an anvil shaft, the anvil shaft being engageable with the trocar. When the anvil is disposed away from the staple and knife housing, the pin end is in a fully extended state and non-engageably disposed towards the medial portion of the adjusting rod.

In another aspect of the present invention, a surgical instrument providing clear indication to a practitioner or user that the device is ready for anastomotic release may include, among other things: a handle assembly having opposed proximal and distal end portions, an upper portion, a lower portion having a gripping portion, and opposed first and second side portions; a rotatable knob disposed at the proximal end portion; an adjusting rod disposed within the handle assembly, the adjusting rod having a proximal portion, an opposed distal portion, and a medial portion disposed thereinbetween, the medial portion having an outer diameter smaller than the outer diameters of the proximal and distal portions the proximal portion of the adjusting rod having a first helical groove and a second helical groove; a projection or thread secured within the housing of the handle assembly and engageable with the first helical groove, whereby rotation of the rotatable knob is configured to advance the adjusting rod in a distal direction within the handle assembly or to retract the adjusting rod in a proximal direction within the handle assembly; a moveable pin disposed at the first side portion of the handle assembly and extending from the first side portion towards the adjusting rod, the pin having a pin end, when in a partially depressed state, is configured to be disposed towards the adjusting rod in a non-engageable configuration.

The surgical instrument of this aspect may further include a proximity sensor disposed or associated with the moveable pin, the proximity sensor may be configured to provide an indication when the moveable pin is proximal to medial portion of the adjusting rod.

The surgical instrument of this aspect may further include: a shaft assembly having a proximal end securably disposed at a distal end of the adjusting rod at the distal end of the handle assembly, a distal end having a staple and knife housing disposed thereat, a sheath disposed between the proximal and distal ends, and a trocar disposed within the sheath and extendable beyond a distal end of the shaft, whereby advancing the adjusting rod advances the trocar and whereby retracting the adjusting rod retracts the trocar; an anvil having an anvil shaft, the anvil shaft being engageable with the trocar; wherein, when the anvil is disposed away from the staple and knife housing, the pin end is in non engageably disposed towards the medial portion of the adjusting rod.

The surgical instrument of this aspect may further include a button associated with the moveable pin, the button extending at least partially through a hole at the first side portion of the handle assembly. The button may have a first position when the pin end is extended and a second position when the pin end is not extended, but in a retracted position. When the button is in the first position, a visual indication may be provided that the surgical instrument is in a configuration for anastomotic release and/or removal from a patient. When in the second position, the button may be extended outside and away from the first side of the handle assembly, and, when in the first position, the button may be partially extended outside and away from the first side of the handle assembly. A top portion of the button may have a first visual indication or color and a side portion of the button disposed away from the top portion may have a second visual indication or color with the first visual indication or color being different from the second visual indication or color; where, when the button is in the first position, only the first visual indication or color of the top portion of the button is visible; and where, when the button is in the second position, both the first visual indication or color of the top portion of the button and second visual indication or color of the side portion are visible.

Thus, clear indications to a practitioner or user that the device is ready for anastomotic release and/or removal from a patient is provided by the present invention.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

DETAILED DESCRIPTION OF THE INVENTION

Figure 1:
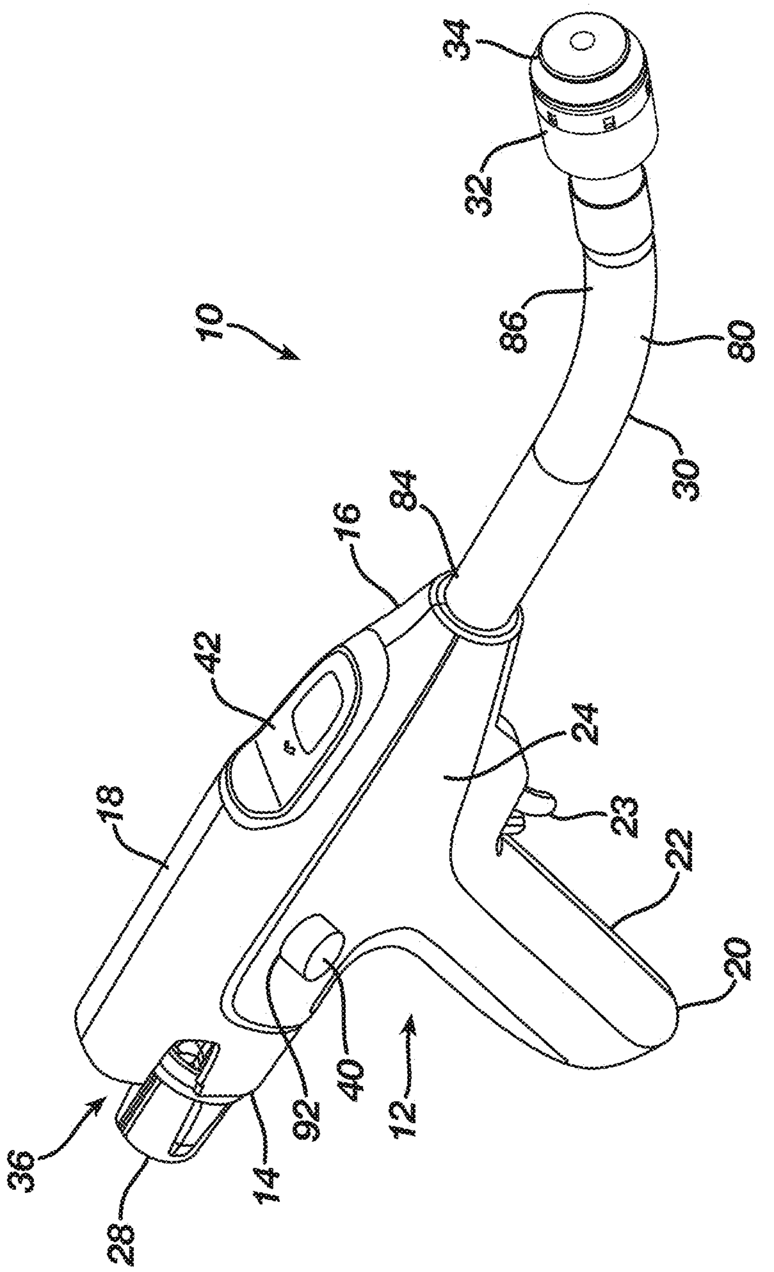
FIG. 1 is a perspective view of the surgical instrument of the present invention.
Figure 3:
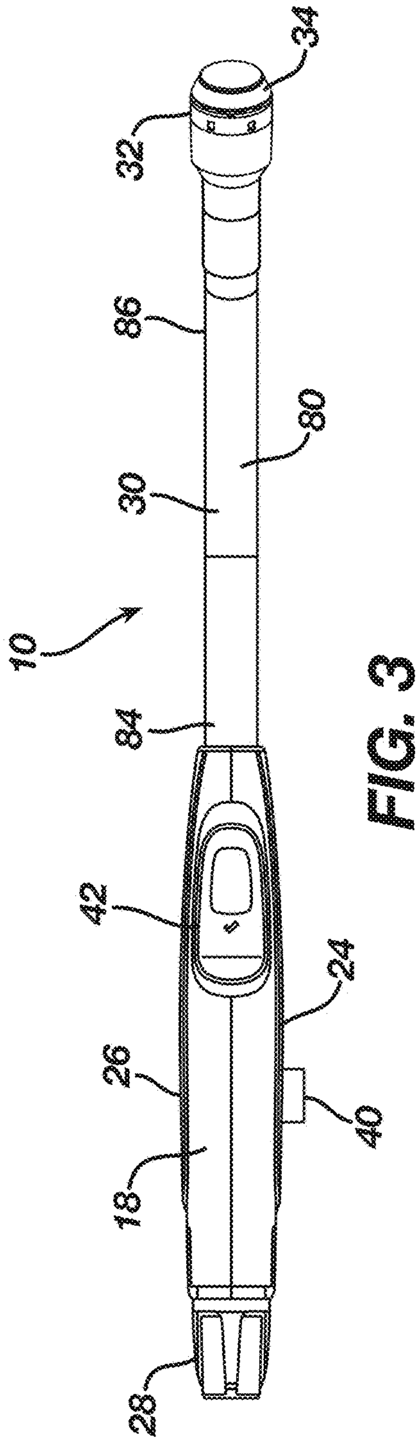
FIG. 3 is a top planar view of the surgical instrument of FIG. 1.
Figure 2:
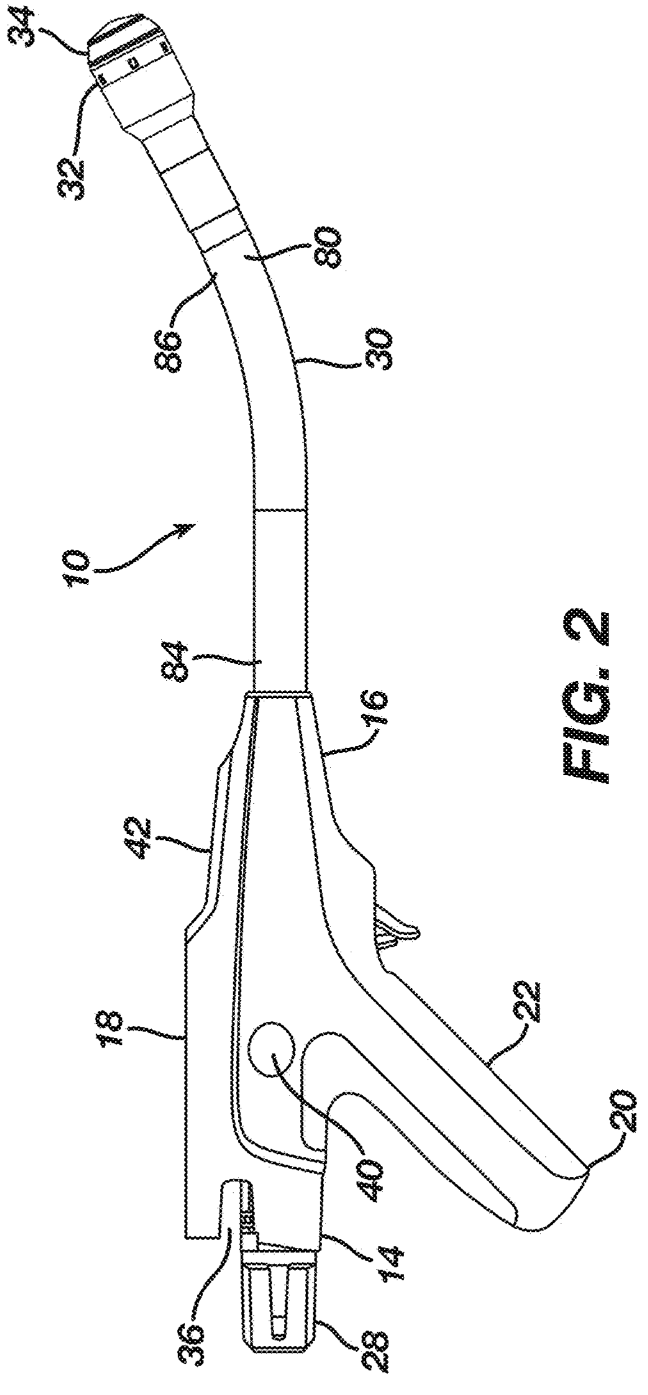
FIG. 2 is a side elevational view of the surgical instrument of FIG. 1.

FIG. 1 is a perspective view of the surgical instrument 10 of the present invention; FIG. 2 is a side elevational view of the surgical instrument 10 of the present invention; and FIG. 3 is a top planar view of the surgical instrument 10 of the present invention. The surgical instrument 10 includes a handle assembly 12, a shaft 30, an end effector assembly 32, and an anvil assembly 34, inter-related as shown. The handle assembly 12 controls the operations of the end effector assembly 32 and of the anvil assembly 34.

The handle assembly 12 includes a proximal end portion 14 of handle assembly 12 and a distal end portion 16 of handle assembly 12. As used herein proximal refers to a direction towards a practitioner or away from a patient, and distal refers to a direction away from a practitioner or towards a patient.

Figure 6:
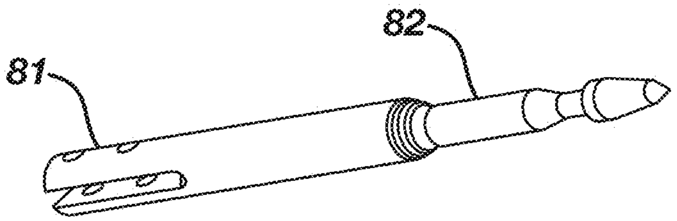
FIG. 6 is a perspective view of a trocar of the surgical instrument of the present invention.

The distal end portion 16 of handle assembly 12 is secured to a proximal end 84 of the shaft 30. A distal end 86 of the shaft 30 is secured to the end effector assembly 32. The proximal end portion 14 of handle assembly 12 includes a rotatable knob 28 and a cavity 36 configured to receive a battery (not shown). The rotatable knob 28 is operably configured to control or adjust movement of the anvil assembly 34 and/or of a trocar 82 (which is depicted in FIG. 6) by select rotation of the rotatable knob 28 by the practitioner. The end effector assembly 32 may be controlled by a firing trigger 23. For example, staples (not shown) in the end effector assembly 32 may be advanced into tissue of a patient by action of the firing trigger 23.

The handle assembly 12 further includes first side portion 24 of handle assembly 12 and an opposed second side portion 26 of handle assembly 12. The first side portion 24 of handle assembly 12 may include a hole 92 through which a button 40 is at least partially disposed in a slidable configuration there through. The button 40 is not limited to a location at the first side portion 24 of handle assembly 12. For example, the button 40 may be suitably disposed at a location at second side portion 26 of handle assembly 12 or even at other locations of the handle assembly 12.

An upper portion 18 of handle assembly 12 includes a status window 42. The status window 42 provides useful indications for proper operation of the surgical instrument 10 to the practitioner. A lower portion 20 of handle assembly 12 includes a grip portion 22 and the firing trigger 23. The grip portion 22 of handle assembly 12 is configured to be grasped by a hand or hands of a practitioner.

Figure 4:
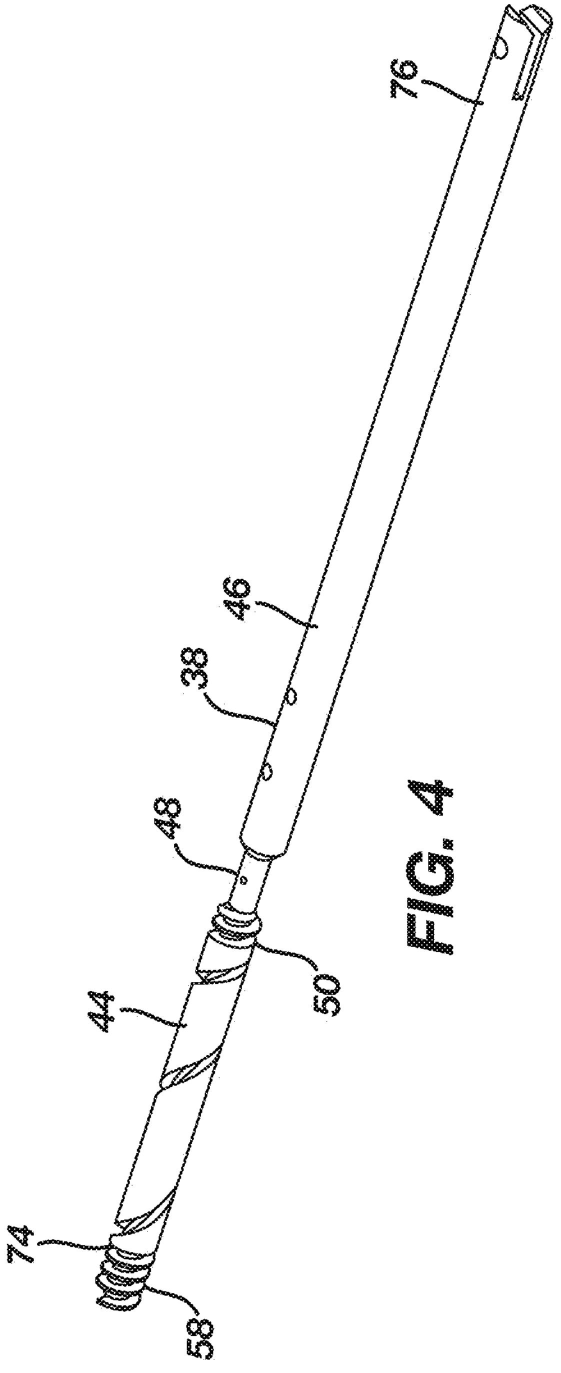
FIG. 4 is a perspective view of an adjusting rod disposed within the surgical instrument of the present invention.
Figure 5:
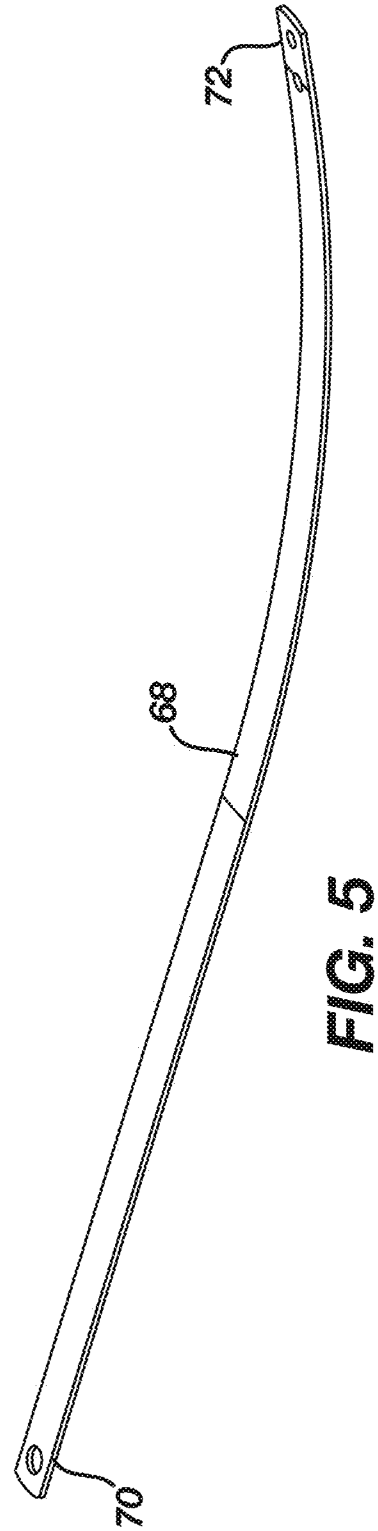
FIG. 5 is a perspective view of shaft assembly disposed within the surgical instrument of the present invention.

Control of the anvil assembly 34 by the rotatable knob 28 at the proximal end portion 14 of handle assembly 12 may be achieved by use of an adjusting rod 38 (which is depicted in FIG. 4), a shaft assembly 68 (which is depicted in FIG. 5), and the trocar 82 (FIG. 6). The adjusting rod 38 includes a proximal portion 44, an opposed distal portion 46, and a medial portion 48 disposed thereinbetween. The proximal end 74 of the adjusting rod 38 includes a first helical groove 58. The first helical groove 58 of the adjusting rod 38 is operatively engageable with the rotatable knob 28 (not shown in FIG. 4). The operation of the second helical groove 50 of the adjusting rod 38 will be described in further detail in conjunction with FIGS. 14-16. The distal end 76 of the adjusting rod 38 is configured to be operatively connected to a proximal end 70 of shaft assembly 68 by use of a connecting member (not shown), such as connecting pin or the like. The adjusting rod 38 is disposed substantially within the handle assembly 12. The shaft assembly 68 is disposed substantially within the shaft 30. The distal end 72 of shaft assembly 68 is configured to be operably connected to a proximal end 81 of the trocar 82 by use of a connecting member (not shown), such as connecting pin or the like. As used herein, the word "operatively' and its variants refer to a functioning or having an effect, either directly or indirectly, of one member on another member. Indirect operatively may include, for example, intermediate components.

Figure 7:
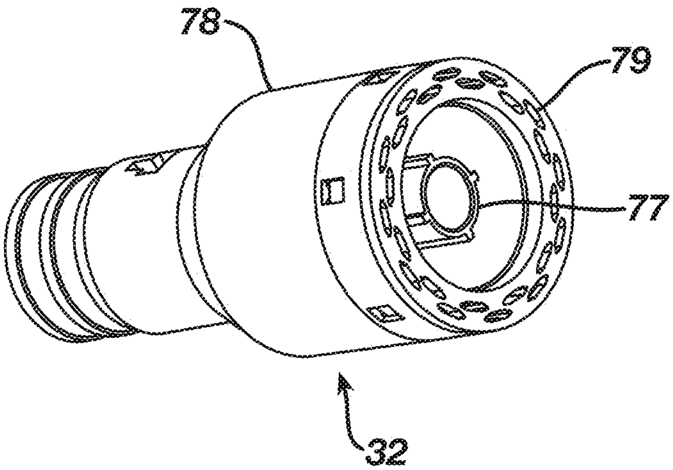
FIG. 7 is a perspective view a staple and knife housing of the surgical instrument of the present invention.

FIG. 7 depicts the end effector assembly 32, which may also be referred to as a staple and knife housing 78. The assembly or housing 32, 78 includes a lumen 77 through which the trocar 82 pass or slide there through and staple housings 79 containing staples (not shown).

Figure 8:
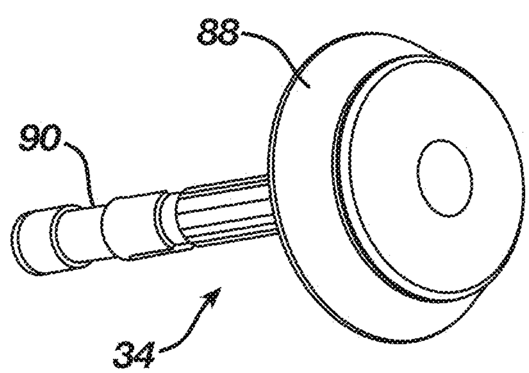
FIG. 8 is a perspective view of an anvil assembly of the surgical instrument of the present invention.
Figure 9:
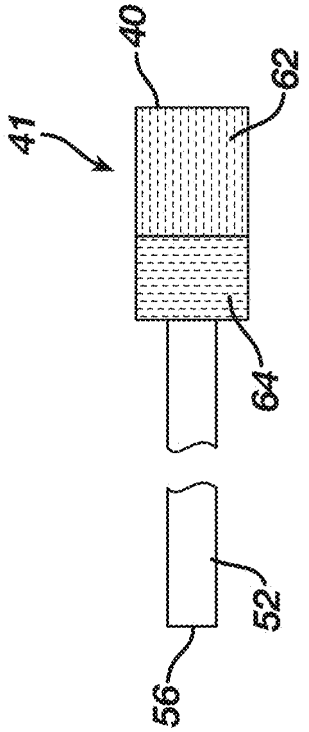
FIG. 9 is a schematic illustration of a button and force-biased extensible pin assembly of the surgical instrument of the present invention.

FIG. 8 depicts the anvil assembly 38 having an anvil 88 connected to an anvil shaft 90. The anvil shaft 90 is releasably engageable with the trocar 82.

Figure 10:
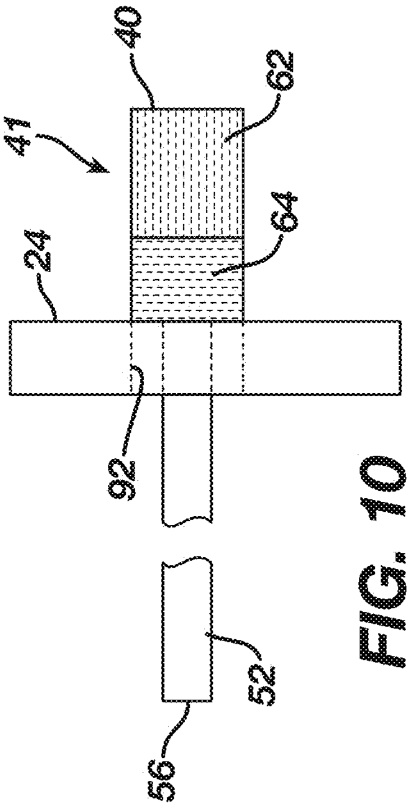
FIG. 10 is a schematic illustration of the button-pin assembly of FIG. 10 where the button is fully extended beyond the housing of the handle assembly of the surgical instrument of the present invention.

FIGS. 9-12 depict button-pin assemblies 41, 41' of the present invention. As depicted in FIG. 10, the button-pin assembly 41 includes the button 40 connected to a pin 52. The pin 52 may be a force-biased, extensible pin. For example, the pin end 56 may be spring biased against the button 40 by an internal spring (not shown), and the pin end 56 is slidably moveable with respect to the button 40. The pin 52 may be made from a plastic material. The button 40 includes a top portion 62 and an opposed bottom or side portion 64. The two portions 62, 64 may include indicia to distinguish one portion from the other portion. The different indicia may be visually distinguishable indicia, such as different colors or patterns. For example, the top portion 62 may be colored green, and the bottom or side portion 64 may be colored red. Such colors are non-limiting, and other combinations of colors, including white, black, blue, red, orange, green violet, etc. may suitably be used.

Figure 11:
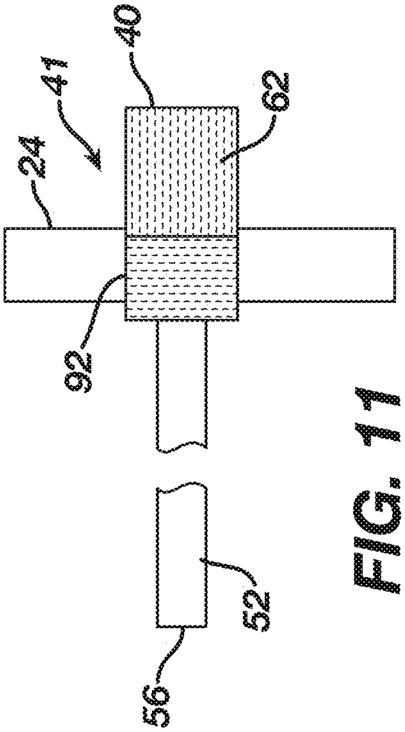
FIG. 11 is a schematic illustration of the button-pin assembly of FIG. 10 where the button is only partially extended beyond the housing of the handle assembly of the surgical instrument of the present invention.

As depicted in FIG. 10, the button-pin assembly may be disposed at the hole 92 at the first side portion 24 of the handle assembly 12, such that at least a portion of the bottom or side portion 64 is slidably disposed through the hole 92. Further, a part or portion of the top portion 62 may also be slidably disposed through the hole 92. As depicted in FIG. 11, the button 40 may be slidably disposed within the hole 92 such that only the top portion 62 or portion thereof is disposed past the hole 92 outside the first side portion 24 of the handle assembly 12.

Figure 12:
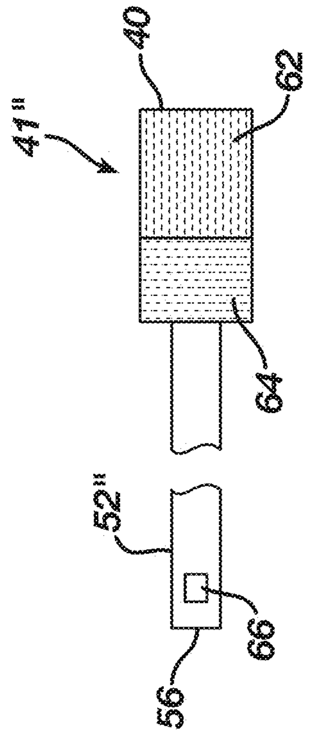
FIG. 12 is a schematic illustration of a button and force-biased extensible pin assembly with a proximity sensor of the surgical instrument of the present invention.

As depicted in FIG. 12, a button-pin assembly 41' may include a proximity sensor 66 within or associated with the pin 52'. The pin 52' may be a force-biased, extensible pin with a spring for pin end/adjusting rod direct contact or may not be such a force-biased, extensible pin, but may have some minor spring force to decompress the button between a compressed state and an uncompressed state. A proximity sensor is a sensor which detects the presence of nearby objects without any physical contact. Useful proximity sensors include, but are not limited to, inductive proximity sensors, optical proximity sensors, capacitive proximity sensors, magnetic proximity sensors, ultrasonic proximity sensors, and the like. The inductive proximity sensors are useful to detect the metallic object which is present next to their active side, and operate under the electrical principal of inductance; where a fluctuating current induces an electromotive force in a target object. The capacitive proximity sensors may detect both metallic and non-metallic targets in powder, granulate, liquid, and solid form. The capacitive proximity sensors use the variance in the capacitance of the sensor to attest that an object has been detected. Magnetic proximity sensors sense the presence of a magnetic object, commonly referred to as the target. The target, characterized by its magnetic field, triggers the switching process; when it enters the detection range of the sensor. Ultrasonic sensors emit an ultrasonic pulse which is reflected by objects in its path and the reflected wave enters the sonic cone. They employ sound waves to detect objects, so color and transparency generally do not affect their operation.

Figure 13A:
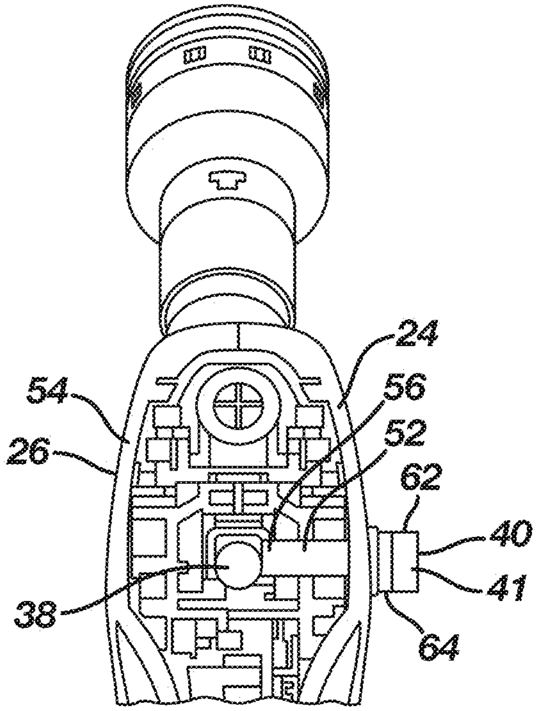
FIGS. 13A and 13B are partial cutaway views of a proximal portion of the handle assembly of the surgical instrument of the present invention.
Figure 13B:
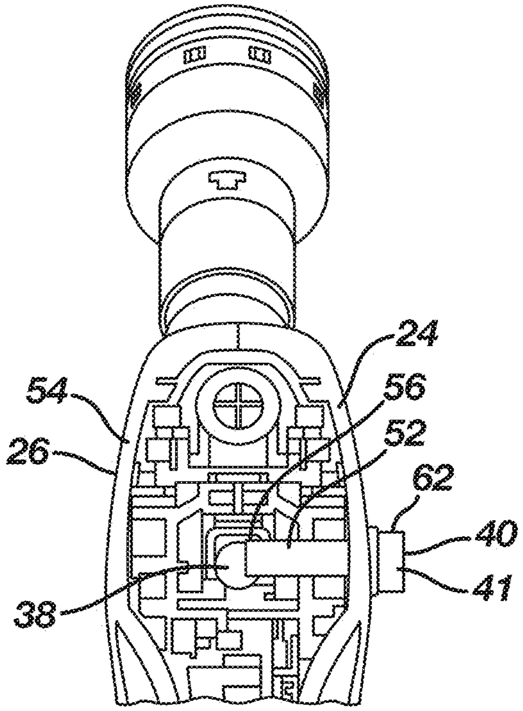

FIGS. 13A and 13B are partial cutaway views of a proximal portion 14 of the handle assembly 12 showing the button-pin assembly 41. The pin 52 is disposed within the housing 54 of the handle assembly 12. The pin end 56 is disposed near the adjusting rod 38. As shown in FIG. 13A, both the top portion 62 and the side portion 64 of the button 40 are disposed outside of the housing 54 at the first side portion 24 of the handle assembly 12. In such a position, the button 40 may be considered in an uncompressed button state where the pin end 56 is forcibly engaging internal structure, such as the adjusting rod 38, of the handle assembly 12. The force exerted by the internal spring (not shown) of the button-pin assembly 41 in such structural engagement of the, for example, the adjusting rod 38, forces the button 40 away from such internal structure and towards the outside of the housing of the handle assembly 12.

As the rotatable knob 28 is rotated, the adjusting rod 38 is translated or laterally moved within the housing 12. Such movement may advance the anvil assembly 34 distally away from the end effector assembly 32. When the pin 52 falls into the necked down, medial portion 48 of the adjusting rod 38 (see, e.g., FIG. 15) the button 40 compresses, making, if desired, an audible "click" sound. As depicted in FIG. 13B, when the button 40 becomes compressed during, for example, anvil assembly 34 extension, the bottom or side portion 64 of the button 40 becomes hidden, i.e., disposed within the housing 54 or the first side portion 24 of the handle assembly. The top portion 62 of the button 40 remains substantially outside of the housing 54. This served as a visual indicator to the practitioner that the surgical instrument 10 is ready to be moved or removed.

Figure 14:
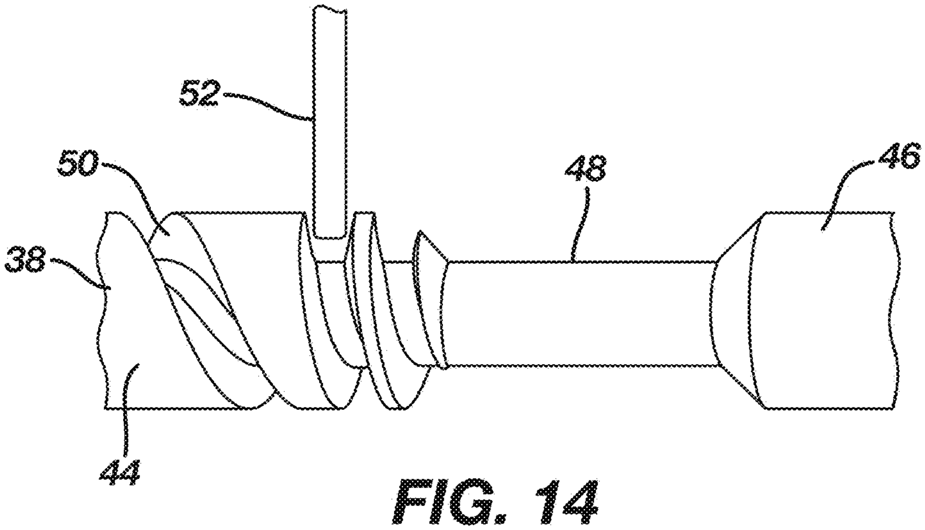
FIG. 14 is a partial view of the adjusting rod of FIG. 4 illustrating engagement of a pin of the button-pin assembly of FIG. 10 at a proximal portion of the adjusting rod.
Figure 15:
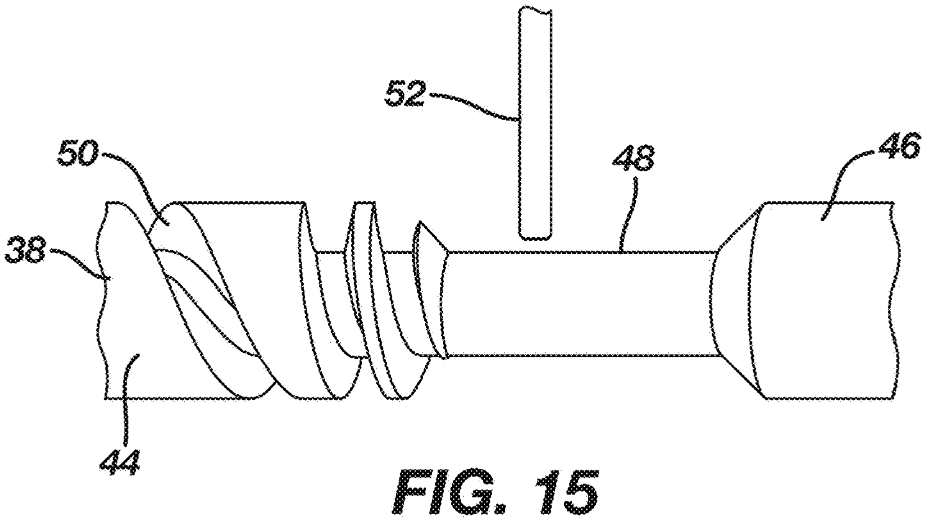
FIG. 15 is a partial view of the adjusting rod of FIG. 4 illustrating engagement of a pin of the button-pin assembly of FIG. 10 at a medial portion of the adjusting rod.
Figure 16:
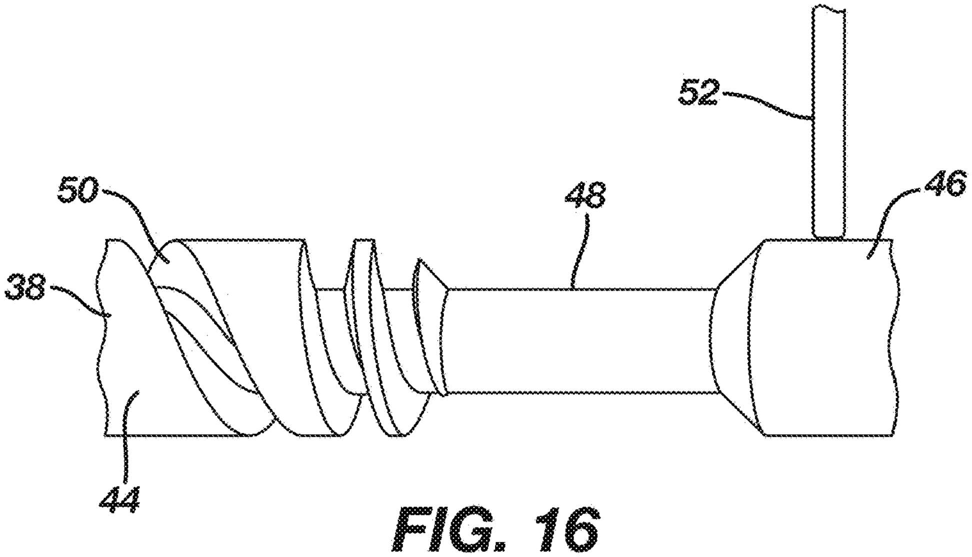
FIG. 16 is a partial view of the adjusting rod of FIG. 4 illustrating engagement of a pin of the button-pin assembly of FIG. 10 at a distal portion of the adjusting rod.

FIGS. 14-16 are partial, side elevational views of the adjusting rod 38 and the pin 52 of the button 40 engaging different portions of the adjusting rod. In FIG. 14 the pin 52 is disposed or engageable within the second helical groove 50 in the proximal portion 44 of the adjusting rod 38. In FIG. 15 the pin 52 is disposed within a medial portion 48 of the adjusting rod 38. The diameter of the medial portion 48 of the adjusting rod 38 is smaller that the diameters of the proximal portion 44 and the distal portion 46 of the adjusting rod 38. The diameter of the proximal portion 44 of the adjusting rod 38 and diameter of the distal portion 46 of the adjusting rod 38 may be the same or different. In FIG. 16 the pin 52 is disposed at the distal portion 46 of the adjusting rod 38. The significances of such arrangements are described in further detail below.

Figure 17:
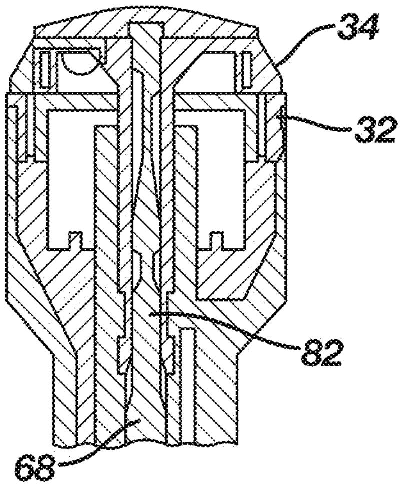
FIG. 17 is a partial cross-sectional view of the end effector and anvil assemblies of the surgical instrument of the present invention being proximately disposed to each other.

FIG. 17 is a partial cross-section view of the end effector assembly 32 and the anvil assembly 34 of the surgical instrument 10 of the present invention. The end effector assembly 32 and the anvil assembly 34 are disposed relatively close to each other. A gap between the anvil assembly 34 and the end effector assembly 32 may be in the order of about 0.035 inches. This dimension of the gap is non-limiting. This anvil position is commonly referred to as a "Low B" position, i.e., a generally or substantially closed position, and generally corresponds to the lowest desired post-firing staple height. In this anvil position the surgical instrument 10 may be fired by, for example, through use of the firing rigger 23, to advance staples from the end effector assembly 32 having the staple housings of the staple and knife housing 78. A firing or multiple firings of the surgical instrument 10 will form an anastomosis at a bodily lumen in which the surgical instrument 10 is disposed.

Figure 18:
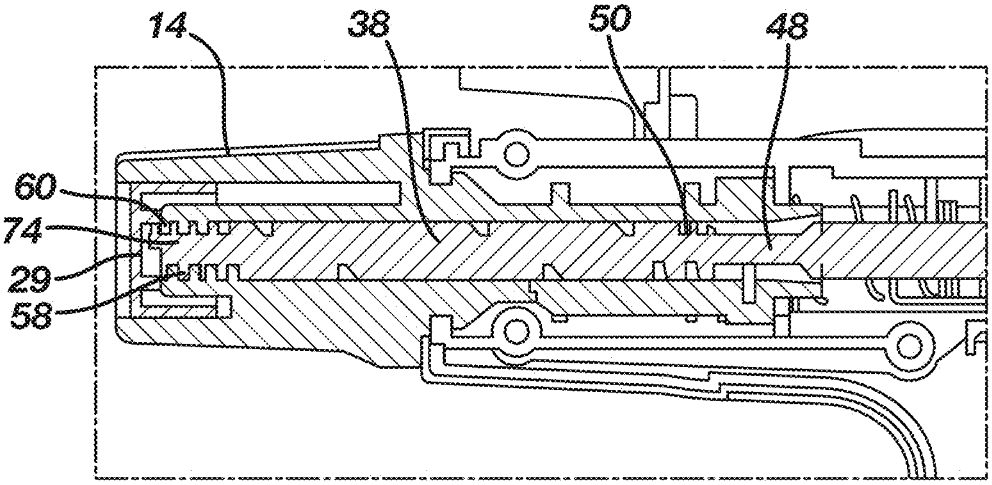
FIG. 18 is a partial cross-sectional view of the handle assembly of the surgical instrument of the present invention showing a position of the adjusting rod therein for a select position of the end effector and anvil assemblies of FIG. 17.

FIG. 18 is a partial cross-sectional view of the handle assembly 12 of the surgical instrument 10 of the present invention showing a position of the adjusting rod 38 therein for the Low B or firing position of the anvil assembly 34 of FIG. 17. The first helical groove 58 of the adjusting rod 38 is engageable with projections or thread 60. The adjusting rod 38 is disposed towards the proximal end portion 14 of handle assembly 12. As depicted in FIG. 18, the proximal end 74 of the adjusting rod 38 may be juxtaposed towards a stop cap 29. The stop cap 29 may be operatively connected to the rotatable knob 28. For ease of illustration, the button-pin assembly 41 is not shown in FIG. 18, but is shown in FIG. 19.

Figure 19:
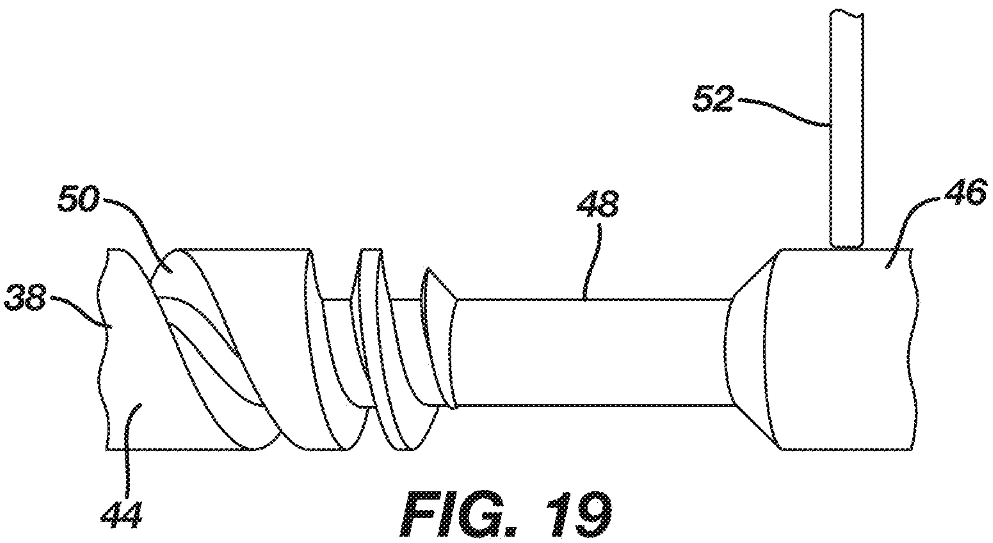
FIG. 19 is a partial view of the adjusting rod of FIG. 4 illustrating engagement of the pin of the button-pin assembly at a distal portion of the adjusting rod for the position of the end effector and anvil assemblies of FIG. 17.

FIG. 19 is a partial view of the adjusting rod 38 illustrating engagement of the pin 52 of the button-pin assembly 41 at a distal portion 46 of the adjusting rod 38 for the position of the end effector and anvil assemblies 32, 34 as illustrated in FIG. 17. In such a position both the top portion 62 and the bottom or side portion 64 of the button 40 are visible, i.e., located outside of the housing 64 of the handle assembly 12 as illustrated in FIG. 13A.

Figure 20:
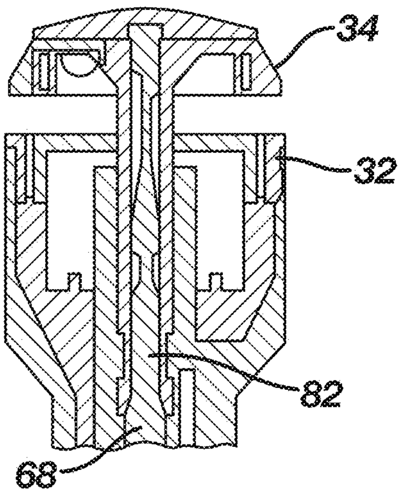
FIG. 20 is a partial cross-sectional view of the end effector and anvil assemblies of the surgical instrument of the present invention being partially displaced from each other.

FIG. 20 is a partial cross-section view of the end effector assembly 32 and the anvil assembly 34 of the surgical instrument 10 of the present invention in an open position. In such an open position, the end effector assembly 32 and the anvil assembly 34 are disposed away from each other. A gap between the anvil assembly 34 and the end effector assembly 32 may be in the order of about 0.215 inches. This dimension of the gap is non-limiting. The anvil assembly 34 is moved away from the end effector assembly 32 via rotation or turning of the rotatable knob 28. For example, rotating the rotatable knob 28 in a counterclockwise direction by two full revolutions, i.e., 2 times 360° or 760°, may move the anvil assembly 34 from the Low B or closed position illustrated in FIG. 17 to the open position illustrated in FIG. 20. In such a case, the pitch of the first helical groove 58 of the adjusting rod 38 may be about 0.090 inches per revolution as the difference between in the gap in FIG. 20 and the gap in FIG. 17 is about 0.180 inches, i.e. 0.216 inches less 0.035 inches. These dimensions are non-limiting, and other dimensions and/or configurations may be used.

Figure 21:
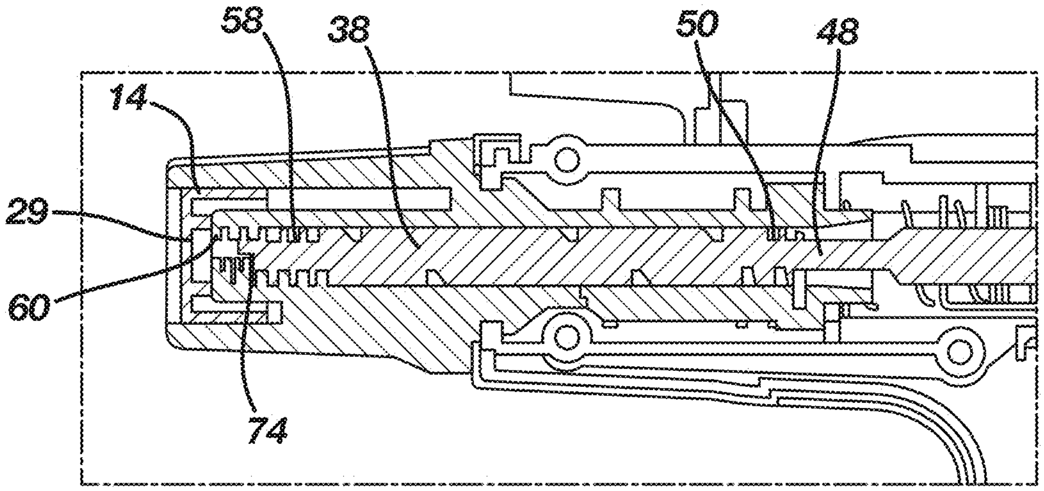
FIG. 21 is a partial cross-sectional view of the handle assembly of the surgical instrument of the present invention showing a position of the adjusting rod therein for the position of the end effector and anvil assemblies of FIG. 20.

FIG. 21 is a partial cross-sectional view of the handle assembly 12 of the surgical instrument 10 of the present invention showing a position of the adjusting rod 38 therein for open position of the anvil assembly 34 of FIG. 20. As the rotatable knob 28 is in operative communication with the adjusting rod 38, in particular with the first helical groove 58 of the adjusting rod 38, rotation of the rotatable knob 28 advances the adjusting rod via the first helical groove 58 of the adjusting rod 38 and the projection or thread 60 arrangement. As depicted in FIG. 21, the adjusting rod 38 is advanced distally by rotation, for example counterclockwise rotation, of the rotatable knob 28 so that the proximal end 74 of the adjusting rod 38 is moved distally away from the stop cap 29 and towards the anvil assembly 34. For ease of illustration, the button-pin assembly 41 is not shown in FIG. 21, but is shown in FIG. 22.

Figure 22:
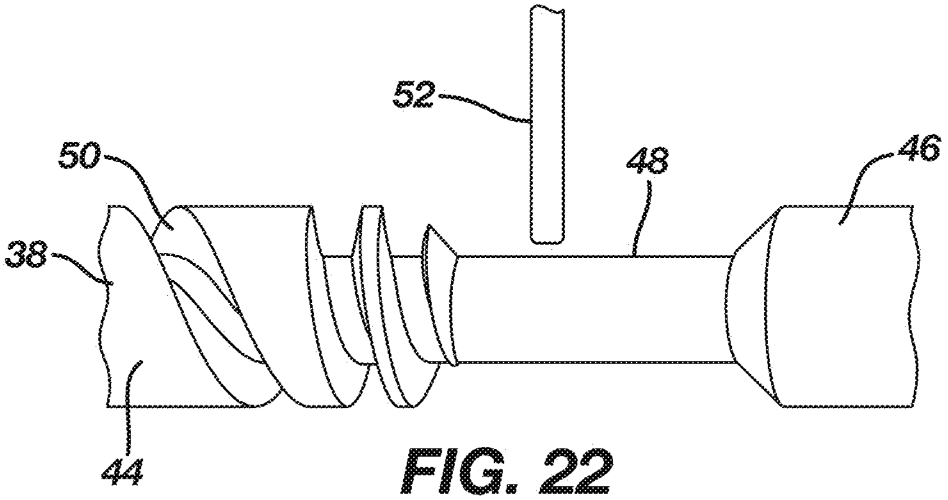
FIG. 22 is a partial view of the adjusting rod of FIG. 4 illustrating engagement of the pin of the button-pin assembly at a medial portion of the adjusting rod for the position of the end effector and anvil assemblies of FIG. 17.

FIG. 22 is a partial view of the adjusting rod 38 illustrating engagement of the pin 52 of the button-pin assembly 41 at a medial portion 48 of the adjusting rod 38 for the position of the end effector and anvil assemblies 32, 34 as illustrated in FIG. 20. In such a position only the top portion 62 of the button 40 is visible, i.e., located outside of the housing 64 of the handle assembly 12 as illustrated in FIG. 13B. If desired, when the pin 52 falls into the necked-down, medial portion 48 of the adjusting rod 38, the button 40 compresses, making, if desired, an audible "click" or other sound. Thus, both an audible and a visual indication of the open positon of the anvil assembly 34 may be provided. In such an open position of the anvil assembly 34 relative to the end effector assembly 32, the surgical instrument may be removed as the anvil assembly 34 and the end effector assembly 32 will be sufficiently clear from the anastomosis formed in position of the anvil assembly 34 and the end effector assembly 32 of FIG. 17.

Figure 23A:
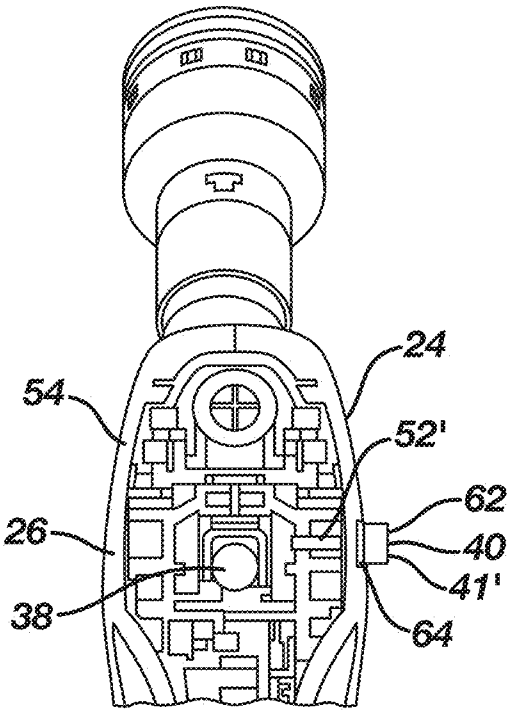
FIGS. 23A and 23B are a partial cutaway views of a proximal portion of the handle assembly of the surgical instrument of the present invention showing different positions of the button-pin assembly of FIG. 13.
Figure 23B:
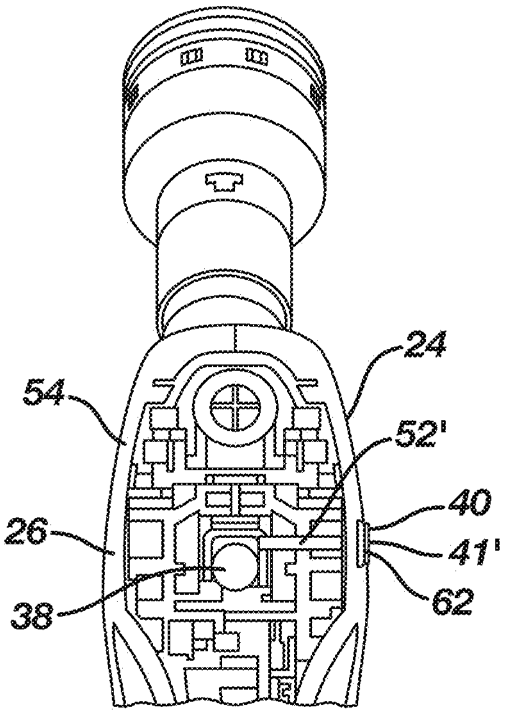

FIGS. 23A and 23B are partial cutaway views of a proximal portion 14 of the handle assembly 12 showing the button-pin assembly 41'. FIGS. 23A and 23B are substantially similar to FIGS. 13A and 13B except that the button-pin assembly 41' having the proximity sensor 66, as described in conjunction with FIG. 12, is illustrated in FIGS. 23A and 23B instead of the button-pin assembly 41 without a proximity sensor. If pin 52' is a force-biased, extensible pin, then pin/adjusting rod integrations will be as discussed above. However, with the use of the proximity sensor 66 the pin 52' need not be such a force-biased, extensible pin for pin/adjusting rod contact.

In FIG. 23A, the button 40 may be pushed from an initial state or position inwardly towards the housing 54 of the handle assembly 12. The button 40 may have both top and side portions with different visual indicators, such as color, as described above or may just have one indication, such as top portion 62.

Figure 24:
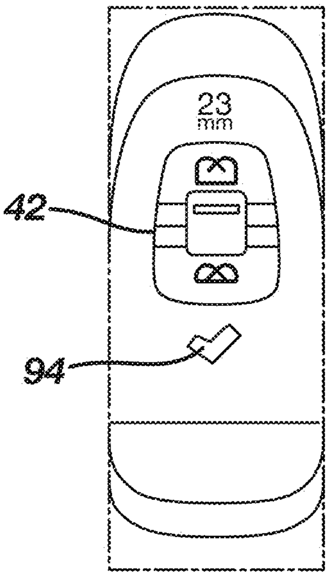
FIG. 24 is an illustration of a status window of the surgical instrument of the present invention.

With the button 40 of the button-pin assembly 41' pushed in, as depicted in FIG. 23B, the proximity sensor 66 of the pin 52' may be disposed within range of the adjusting rod 38. As the rotatable knob 28 is rotated, the adjusting rod 38 translates or laterally moves within the handle assembly 12. For example, counterclockwise rotation of the rotatable knob 28 may distally advance the adjusting rod 39 (and correspondingly the anvil assembly 34), and clockwise rotation of the rotatable knob 28 may proximately retract the adjusting rod 39 (and correspondingly the anvil assembly 34). When the proximity sensor 66 identifies that the adjusting rod 38 has translated a sufficient amount, for example to the open position of the anvil assembly 34 as described above in conjunction with FIG. 20, an indication 94 may be presented in the status window 42, as depicted in FIG. 24. Such an indication 94 will signal to a practitioner that the device is ready for anastomotic release or removal of the surgical instrument may commence. The indication 94 become visible by lighting-up or illuminating, could change color, blink continuously, etc. to indicate the anvil assembly 34 is now fully opened the desired amount and ready for anastomotic release.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The following aspects, embodiments, and the like of the invention or inventive technology, which are labelled as clauses below, are part of the detailed description for the present invention and may be combined in any fashion and combination and be within the scope of the present invention, as follows:

Clause 1. A surgical instrument (10) comprising:

a handle assembly (12) having opposed proximal and distal end portions (14, 16), an upper portion (18), a lower portion (20) having a gripping portion (22), and opposed first and second side portions (24, 26);

a rotatable knob (28) disposed at the proximal end portion (14);

an adjusting rod (38) disposed within the handle assembly (12), the adjusting rod (38) having a proximal portion (44), an opposed distal portion (46), and a medial portion (48) disposed thereinbetween, the medial portion (48) having an outer diameter smaller than the outer diameters of the proximal and distal portions (44, 46), the proximal portion (44) of the adjusting rod (38) having a first helical groove (58) and a second helical groove (50);

a projection (60) secured within the housing (54) of the handle assembly (12) and engageable with the first helical groove (58), whereby rotation of the rotatable knob (28) is configured to advance the adjusting rod (38) in a distal direction within the handle assembly (12) or to retract the adjusting rod (38) in a proximal direction within the handle assembly (12);

a button (40) disposed at the first side portion (24), the button having a force-biased, extensible pin (52) extending towards the adjusting rod (38), the pin (52) having a pin end (56), when in a partially extended state, is configured to be engageably disposed with the distal portion (46) of the adjusting rod (38), and the pin end (56), when in a fully extended state, is configured to be proximally disposed towards the medial portion (48) of the adjusting rod (38).

Clause 2. The surgical instrument (10) of clause 1, wherein the button (40) has a first position when the pin end (56) is extended and a second position when the pin end (56) is not extended, but in a retracted position.

Clause 3. The surgical instrument (10) of clause 2 or any preceding clauses, wherein, when the button (40) is in the first position, a visual indication is provided that the surgical instrument is in a configuration for removal from a patient.

Clause 4. The surgical instrument (10) of clause 1 or any preceding clauses, wherein, when in the second position, the button is extended outside and away from the first side (24) of the handle assembly (12), and wherein, when in the first position, the button (40) is partially extended outside and away from the first side (24) of the handle assembly (12).

Clause 5. The surgical instrument (10) of clause 4 or any preceding clauses, wherein a top portion (62) of the button (40) has a first color and a side portion (64) of the button disposed away from the top portion (62) has a second color with the first color being different from the second color; wherein, when the button (40) is in the first position, only the first color of the top portion (62) of the button (40) is visible; and wherein, when the button (40) is in the second position, both the first color of the top portion (62) of the button (40) and second color of the side portion (64) are visible.

Clause 6. The surgical instrument (10) of clause 1 or any preceding clauses, further comprising a proximity sensor (66) disposed within the handle assembly (12), the proximity sensor (66) configured to provide an indication when the pin (52') is in the fully extended state.

Clause 7. The surgical instrument (10) of clause 6 or any preceding clauses, wherein the upper portion (18) of the handle assembly (12) further comprises an indicator status window (42), and wherein the indication that the pin (52') is in the fully extended state is displayed in the indicator status window (42).

Clause 8. The surgical instrument (10) of clause 1 or any preceding clauses, further comprising:

a shaft assembly (68) having a proximal end (70) securably disposed at a distal end (76) of the adjusting rod (38) at the distal end 16 of the handle assembly (12), a distal end (72) having a staple and knife housing (78) disposed thereat, a sheath (80) disposed between the proximal and distal ends (68, 70), and a trocar (82) disposed within the sheath (80) and extendable beyond a distal end (86) of the shaft (30), wherein advancing the adjusting rod (38) advances the trocar (82) and wherein retracting the adjusting rod (38) retracts the trocar (82);

an anvil (88) having an anvil shaft (90), the anvil shaft (90) being engageable with the trocar (82);

wherein, when the anvil (88) is disposed away from the staple and knife housing (78), the pin end (56) is in a fully extended state and non-engageably disposed towards the medial portion (48) of the adjusting rod (38).

Clause 9. A surgical instrument (10) comprising:

a handle assembly (12) having opposed proximal and distal end portions (14, 16), an upper portion (18), a lower portion (20) having a gripping portion (22), and opposed first and second side portions (24, 26);

a rotatable knob (28) disposed at the proximal end portion (14);

an adjusting rod (38) disposed within the handle assembly (12), the adjusting rod (38) having a proximal portion (44), an opposed distal portion (46), and a medial portion (48) disposed thereinbetween, the medial portion (48) having an outer diameter smaller than the outer diameters of the proximal and distal portions (44, 46), the proximal portion (44) of the adjusting rod (38) having a first helical groove (58) and a second helical groove (50);

a projection secured within the housing (54) of the handle assembly (12) and engageable with the first helical groove (58), whereby rotation of the rotatable knob (38) is configured to advance the adjusting rod (38) in a distal direction within the handle assembly (12) or to retract the adjusting rod (38) in a proximal direction within the handle assembly (12);

a moveable pin (52') disposed at the first side portion (24) of the handle assembly and extending from the first side portion (24) towards the adjusting rod (38), the pin (52') having a pin end (54), when in a partially depressed state, is configured to be disposed towards the adjusting rod (38) in a non-engageable configuration.

Clause 10. The surgical instrument (10) of clause 9, further comprising a proximity sensor (66) disposed associated with the moveable pin (52'), the proximity sensor (66) configured to provide an indication when the moveable pin (52') is proximal to medial portion (48) of the adjusting rod (38).

Clause 11. The surgical instrument (10) of clause 10, wherein the upper portion (18) of the handle assembly (12) further comprises an indication (94) in a status window (42), and wherein the indication (94) that signals that the moveable pin (52') is proximal to medial portion (48) of the adjusting rod (38).

Clause 12. The surgical instrument (10) of clause 9 or any preceding clauses 9-11, further comprising:

a shaft assembly (68) having a proximal end (70) securably disposed at a distal end (76) of the adjusting rod (38) at the distal end 16 of the handle assembly (12), a distal end (72) having a staple and knife housing (78) disposed thereat, a sheath (80) disposed between the proximal and distal ends (68, 70), and a trocar (76) disposed within the sheath (74) and extendable beyond a distal end (86) of the shaft (30), wherein advancing the adjusting rod (38) advances the trocar (82) and wherein retracting the adjusting rod (38) retracts the trocar (82);

an anvil (88) having an anvil shaft (90), the anvil shaft (90) being engageable with the trocar (82);

wherein, when the anvil (88) is disposed away from the staple and knife housing (78), the pin end (56) is in non-engageably disposed towards the medial portion (48) of the adjusting rod (38).

Clause 13. The surgical instrument (10) of clause 9 or any preceding clauses 9-12, further comprising:

a button (40) associated with the moveable pin (52'), the button (40) extending at least partially through a hole (92) at the first side portion (24) of the handle assembly (12).

Clause 14. The surgical instrument (10) of clause 13 or any preceding clauses 9-13, wherein the button (40) has a first position when the pin end (56) is extended and a second position when the pin end (56) is not extended, but in a retracted position.

Clause 15. The surgical instrument (10) of clause 14 or any preceding clauses 9-14, wherein, when the button (40) is in the first position, a visual indication is provided that the surgical instrument is in a configuration for removal from a patient.

Clause 16. The surgical instrument (10) of clause 13 or any preceding clauses 9-15, wherein, when in the second position, the button (40) is extended outside and away from the first side (24) of the handle assembly (12), and wherein, when in the first position, the button (40) is partially extended outside and away from the first side (24) of the handle assembly (12).

Clause 17. The surgical instrument (10) of clause 16 or any preceding clauses 9-16, wherein a top portion (62) of the button (40) has a first color and a side portion (64) of the button disposed away from the top portion (62) has a second color with the first color being different from the second color; wherein, when the button (40) is in the first position, only the first color of the top portion (62) of the button (40) is visible; and wherein, when the button (40) is in the second position, both the first color of the top portion (62) of the button (40) and second color of the side portion (64) are visible.

What is claimed is:

1. A surgical instrument comprising:

a handle assembly having opposed proximal and distal end portions an upper portion, a lower portion having a gripping portion, and opposed first and second side portions;

a rotatable knob disposed at the proximal end portion;

an adjusting rod disposed within the handle assembly, the adjusting rod having a proximal portion, an opposed distal portion, and a medial portion disposed thereinbetween, the medial portion having an outer diameter smaller than the outer diameters of the proximal and distal portions the proximal portion of the adjusting rod having a first helical groove and a second helical groove;

a projection or thread secured within the housing of the handle assembly and engageable with the first helical groove, whereby rotation of the rotatable knob is configured to advance the adjusting rod in a distal direction within the handle assembly or to retract the adjusting rod in a proximal direction within the handle assembly;

a button disposed at the first side portion, the button having a force-biased, extensible pin extending towards the adjusting rod, the pin having a pin end, when in a partially extended state, is configured to be engageably disposed with the distal portion of the adjusting rod, and the pin end, when in a fully extended state, is configured to be proximally disposed towards the medial portion of the adjusting rod.

2. The surgical instrument of claim 1, wherein the button has a first position when the pin end is extended and a second position when the pin end is not extended, but in a retracted position.

3. The surgical instrument of claim 2, wherein, when the button is in the first position, a visual indication is provided that the surgical instrument is in a configuration for removal from a patient.

4. The surgical instrument of claim 1, wherein, when in the second position, the button is extended outside and away from the first side of the handle assembly, and wherein, when in the first position, the button is partially extended outside and away from the first side of the handle assembly.

5. The surgical instrument of claim 4, wherein a top portion of the button has a first color and a side portion of the button disposed away from the top portion has a second color with the first color being different from the second color; wherein, when the button is in the first position, only the first color of the top portion of the button is visible; and wherein, when the button is in the second position, both the first color of the top portion of the button and second color of the side portion are visible.

6. The surgical instrument of claim 1, further comprising a proximity sensor disposed within the handle assembly, the proximity sensor configured to provide an indication when the pin is in the fully extended state.

7. The surgical instrument of claim 6, wherein the upper portion of the handle assembly further comprises an indicator status window, and wherein the indication that the pin is in the fully extended state is displayed in the indicator status window.

8. The surgical instrument of claim 1, further comprising:

a shaft assembly having a proximal end securably disposed at a distal end of the adjusting rod at the distal end of the handle assembly, a distal end having a staple and knife housing disposed thereat, a sheath disposed between the proximal and distal ends, and a trocar disposed within the sheath and extendable beyond a distal end of the shaft, wherein advancing the adjusting rod advances the trocar and wherein retracting the adjusting rod retracts the trocar;

an anvil having an anvil shaft, the anvil shaft being engageable with the trocar;

wherein, when the anvil is disposed away from the staple and knife housing, the pin end is in a fully extended state and non-engageably disposed towards the medial portion of the adjusting rod.

9. A surgical instrument comprising:

a handle assembly having a proximal end portion, a distal end portion opposite the proximal end portion, an upper portion, a lower portion having a gripping portion, a first side portion, and a second side portion opposite the first side portion;

a rotatable knob disposed at the proximal end portion;

an adjusting rod disposed within the handle assembly, the adjusting rod having a proximal portion, an opposed distal portion, and a medial portion disposed therein-between, the medial portion having an outer diameter smaller than the outer diameters of the proximal and distal portions, the proximal portion of the adjusting rod having a first helical groove and a second helical groove;

a projection secured within the housing of the handle assembly and engageable with the first helical groove, whereby rotation of the rotatable knob is configured to advance the adjusting rod in a distal direction within the handle assembly or to retract the adjusting rod in a proximal direction within the handle assembly;

a moveable pin disposed at the first side portion of the handle assembly and extending from the first side portion towards the adjusting rod, the pin having a pin end, when in a partially depressed state, the movable pin is configured to be disposed towards the adjusting rod in a non-engageable configuration.

10. The surgical instrument of claim 9, further comprising a proximity sensor disposed or associated with the moveable pin, the proximity sensor configured to provide an indication when the moveable pin is proximal to medial portion of the adjusting rod.

11. The surgical instrument of claim 9, further comprising:

a shaft assembly having a proximal end securably disposed at a distal end of the adjusting rod at the distal end of the handle assembly, a distal end having a staple and knife housing disposed thereat, a sheath disposed between the proximal and distal ends, and a trocar disposed within the sheath and extendable beyond a distal end of the shaft, wherein advancing the adjusting rod advances the trocar and wherein retracting the adjusting rod retracts the trocar;

an anvil having an anvil shaft, the anvil shaft being engageable with the trocar;

wherein, when the anvil is disposed away from the staple and knife housing, the pin end is in non-engageably disposed towards the medial portion of the adjusting rod.

12. The surgical instrument of claim 9, further comprising:

a button associated with the moveable pin, the button extending at least partially through a hole at the first side portion of the handle assembly.

13. The surgical instrument of claim 12, wherein the button is movable between a first position when the pin end is extended and a second position when the pin end is in a retracted position.

14. The surgical instrument of claim 13, wherein, when the button is in the first position, a visual indication is provided that the surgical instrument is in a configuration for removal from a patient.

15. The surgical instrument of claim 13, wherein, when in the second position, the button extends outside and away from the first side of the handle assembly, and wherein, when in the first position, the button extends partially outside and away from the first side of the handle assembly.

16. The surgical instrument of claim 13, wherein a top portion of the button has a first color and a side portion of the button extending away from the top portion has a second color different than the first color; wherein, when the button is in the first position, only the first color of the top portion of the button is visible; and wherein, when the button is in the second position, both the first color of the top portion of the button and the second color of the side portion are visible.

* * * * *